United States Patent [19]

Fujiwara et al.

[11] Patent Number: 4,880,926

[45] Date of Patent: Nov. 14, 1989

[54] OPTICAL RESOLUTION OF BENZOXAZINES

[75] Inventors: Toshihiro Fujiwara; Hideaki Tsurumi; Yukio Sato, all of Tokyo, Japan

[73] Assignee: Daiichi Seiyaku Co., Ltd., Tokyo, Japan

[21] Appl. No.: 227,925

[22] Filed: Aug. 3, 1988

[30] Foreign Application Priority Data

Aug. 3, 1987 [JP] Japan .................................. 62-194017
Aug. 3, 1987 [JP] Japan .................................. 62-194018

[51] Int. Cl.$^4$ ............................................ C07D 265/36
[52] U.S. Cl. .................................................... 544/105
[58] Field of Search ........................................... 544/105

[56] References Cited

U.S. PATENT DOCUMENTS 2,381,935 8/1945 Strain et al. .......................... 544/105

FOREIGN PATENT DOCUMENTS 0047005 8/1981 European Pat. Off. .
1809454 7/1970 Fed. Rep. of Germany .

OTHER PUBLICATIONS

Monatshefte Fur Chemie, vol. 110, No. 2, pp. 257–265 (1979).
Reagents for Organic Synthesis, L. F. Fieser et al., vol. 1, pp. 108–109 (1967).
Houben-Weyl, Methoden Der Organischen Chemie, vol. VI, Part 4, pp. 555–560 (1966).

Patent Abstracts of Japan, vol. 11, No. 297, p. (C-488)(2744)(Sep. 1987).
"Asymmetrical Nonbridgehead Nitrogen-XXIV"-By R. G. Kostyanowsky et al., Tetrahedron, 38 949 (1982).
"Analysis of Permeation Profiles of Drugs From Systems Containing Micelles" by K. Juni et al., Chemical Pharmaceutical Bulletin, 26, 883 (1978).

Primary Examiner—Richard L. Raymond
Attorney, Agent, or Firm—Sughrue, Mion, Zinn, Macpeak & Seas

[57] ABSTRACT

The invention relates to a process for producing a (±)-3-alkyl-3,4-dihydro-2H-[1,4]benzoxazine derivate of formula (II) by stepwise racemization procedure.

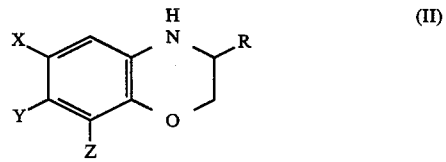

The invention further provides a process for optical resolution through the formation of a salt between a (±)-benzoxazine compound and an optically active form of camphor-10-sulfonic acid. Without requiring the conventional expensive resolution reagents, this process not only assures production of an optically active isomer of compound (II) in high purity but also permits reuse of the optical resolution reagent.

4 Claims, 1 Drawing Sheet

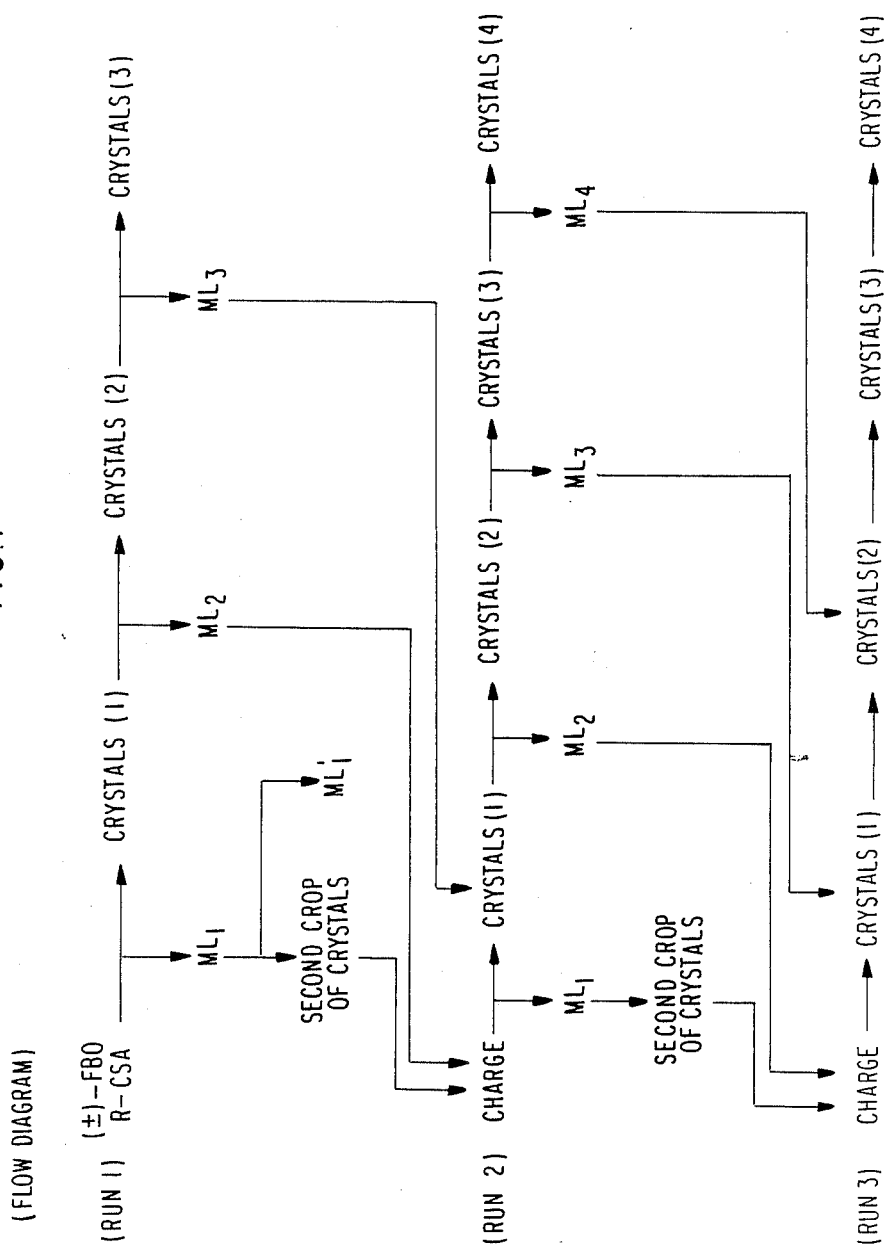

OPTICAL RESOLUTION OF BENZOXAZINES

FIELD OF THE INVENTION

The present invention relates, in one aspect, to a process for producing (±)-3-alkyl-3,4-dihydro-2H-[1,4]benzoxazine derivatives and, in another aspect, to a process for producing optically active 3-alkyl-3,4-dihydro-2H-[1,4]benzoxazine derivatives, especially (S)-3-alkyl-benzoxazine derivatives.

BACKGROUND OF THE INVENTION

As processes for producing an optical isomer of compound (II)

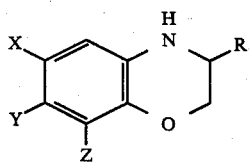

wherein X, Y and Z, which may be the same or different, each represents a hydrogen atom or a halogen atom and R represents a lower alkyl group having 1 to 6 carbon atoms, a process comprising converting compound (II) into an optically active proline derivative and isolating said product is known as described, for example, in EP-A-206,283. However, this procedure is disadvantageous in that the resolution reagent proline is expensive and is difficult to use again. Another known process involves the use of an asymmetric hydrolytic enzyme as described, for example, in JP-A-62-87577 (the term "JP-A" as used herein refers to a "published unexamined Japanese patent application") and EP-A-206,283.

SUMMARY OF THE INVENTION

The present invention relates, in a first aspect, to a process for producing a (±)-3-alkyl-3,4-dihydro-2H-[1,4]benzoxazine derivative of general formula (II)

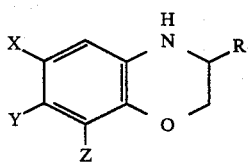

wherein X, Y and Z, which may be the same or different, each represents a hydrogen atom or a halogen atom and R represents a lower alkyl group having 1 to 6 carbon atoms, which comprises hydrogenating a 3-alkyl-2H-[1,4]-benzoxazine derivative of general formula (I)

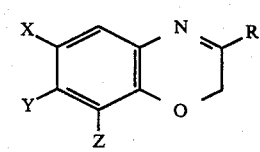

wherein X, Y, Z and R have the same meanings as defined above.

The invention further relates to a process for producing a (±)-3-alkyl-3,4-dihydro-2H-[1,4]benzoxazine derivative of general formula (II) which comprises: dehydrogenating an (R)-(+)-3-alkyl-3,4-dihydro-2H-[1,4]-benzoxazine derivative of general formula (III)

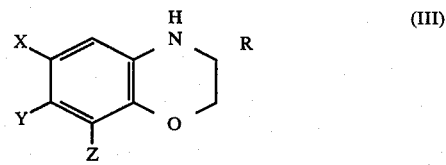

wherein X, Y and Z, which may be the same or different, each represents a hydrogen atom or a halogen atom and R represents a lower alkyl group having 1 to 6 carbon atoms to give a 3-alkyl-2H-[1,4]benzoxazine derivative of general formula (I), wherein X, Y, Z and R have the same meanings as defined above; and hydrogenating the compound (I).

Further, this invention relates, in a second aspect, to the optical resolution of a (±)-3-alkyl-3,4-dihydro-2H-[1,4]benzoxazine derivative of general formula (II). Namely, the invention is directed to the salts of an (S)-3-alkyl-benzoxazine derivative and an (R)-(−)-camphor-10-sulfonic acid which has the general formula (V)'

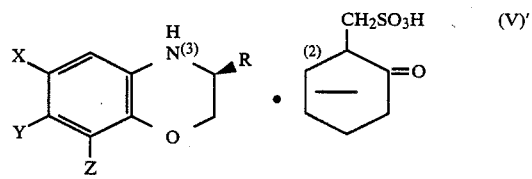

wherein X, Y and Z, which may be the same or different, each represents a hydrogen atom or a halogen atom and R represents a lower alkyl group having 1 to 6 carbon atoms; and it is also directed to a process for producing an optically active benzoxazine derivative which comprises subjecting a (±)-3-alkyl-3,4-dihydro-2H-[1,4]-benzoxazine compound of general formula (II)

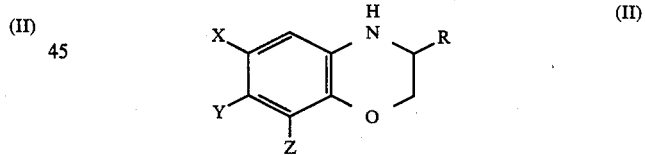

wherein X, Y and Z, which may be the same or different, each represents a hydrogen atom or a halogen atom and R represents a lower alkyl group having 1 to 6 carbon atoms, to an optical resolution using an optically active isomer of camphor-10-sulfonic acid (IV) as a resolution agent.

7,8-Difluoro-3-methyl-3,4-dihydro-2H-[1,4]-benzoxazine, which corresponds to the compound of formula (II) wherein X is a hydrogen atom, Y and Z each is a fluorine atom and R is a methyl group, is of value as an intermediate for the production of various compounds having potent antibacterial activity, such as ofloxacin (see, for example, Japanese Patent No. 1,444,043 and U.S. Pat. No. 4,382,892).

Furthermore, the resulting optically active compound is also useful as an intermediate for the production of, for example, (S)-(−)-9-fluoro-3-methyl-10-(4-methyl-1-piperadinyl)-7-oxo-2,3-dihydro-7H-pyrido-

[1,2,3-de][1,4]benzoxazine-6-carboxylic acid (see, for example, JP-A-62-87577 and EP-A-206,283).

The present invention provides useful processes in that the optically active form of compound (II) can be produced with efficiency and high purity by the simple procedure of recrystallization employing less expensive optical resolution reagent and in that the optical resolution reagent can be used many times.

The present invention also provides a useful process of converting undesirable (R)-isomer of compound (II) into the racemic mixture. Through the combination of the optical resolution method of compound (II) and the racemization procedure of undesirable-isomer, the yield of useful (S)-isomer of compound (II) is increased.

BRIEF DESCRIPTION OF THE ACCOMPANYING DRAWING

FIG. 1 is a recrystallization flow diagram.

DETAILED DESCRIPTION OF THE INVENTION

The first aspect of the present invention is described in detail below.

For the purpose of utilizing the undesirable (R)-isomer of compound (II), the present inventors found that compound (I) was obtained by the dehydrogenation of (R)-isomer of compound (II), and from this compound (I), racemic compound (II) was reproducible through the hydrogenation.

The dehydrogenation reaction for conversion of compound (III) to compound (I) is carried out by treating compound (III) with a halogenating agent and a base in the presence or absence of a solvent at a temperature from about −100° C. to room temperature, preferably at −80° to 10° C., for a period of about 1 to 120 minutes.

The above-mentioned base may be organic or inorganic, and the preferred base is an aliphatic tertiary amine such as trimethylamine, triethylamine, tripropylamine, N,N-diisopropylethylamine and so on. The base may be used in virtually any desired proportion not less than equimolar with respect to compound (III) and may be used as a solvent of the reaction.

The halogenating agent may be virtually any known halogenating agent, such as chlorine, bromine, sulfuryl chloride, N-chlorosuccinimide (NCS), N-bromosuccinimide (NBS), N-bromoacetamide, hypochlorous acid, hypobromous acid, t-butyl hypochlorite and so on.

The amount of the halogenating agent is also any desired except that it must be at least equimolar to compound (III), and is preferably 1 to 10 mols per mol of compound (III).

Typical examples of the solvent that can be used in this reaction include various solvents which are insert to the reaction, such as esters (e.g., ethyl acetate, propyl acetate, etc.), amides (e.g., N,N-dimethylformamide, N,N-dimethylacetamide, etc.), ethers (e.g., tetrahydrofuran, 1,4-dioxane, etc.) and so on. The solvent is generally used in the range of 0 to 50 parts by weight with respect to compound (III).

The compound (I) which forms by the dehydrogenation of compound (III) can be isolated as pure crystals by the known procedures such as recrystallization, silica gel chromatography, etc., but the hydrogenation reaction may be conducted without isolating compound (I).

The hydrogenation of compound (I) to compound (II) can be carried out by the known procedure per se, for example, by reduction using a metal hydride such as sodium borohydride, lithium borohydride, etc., or by catalytic hydrogenation using a catalyst such as palladium-on-carbon, platinum, Raney nickel, etc.

After completion of the hydrogenation, compound (II) can be isolated and purified by the known method such as extraction, redistribution, concentration, crystallization, chromatography and so on.

In the course of isolation and purification, the use of ordinary acid, such as hydrochloric acid, sulfuric acid, nitric acid, etc., in a proportion not less than equimolar with respect to compound (II) results in the direct crystallization and recovery of the corresponding salt of compound (II).

The optical purity (% e.e.) of compound (II) or compound (III) was determined by the following procedure. The "% e.e." is an abbreviation for % enantiomer excess, and is a measure of an optical purity of an optically active compound (see, for example, Asymmetric Synthesis, Vol. 1, p. 45, 60, Academic Press, N.Y. (1983), edited by J. D. Morrison et al.) For example, the "% e.e." is calculated as follows:

$$\frac{(R) - (S)}{(R) + (S)} \times 100 \text{ (an equation for } (R)\text{-isomer)}$$

wherein (R) represents a molar ratio of (R)-isomer in percent, and (S) represents that of the (S)-isomer, when (R)+(S) is taken as 100%. Namely, in 0.5 ml of tetrahydrofuran was dissolved 20 mg of compound (II) or (III), followed by addition of 17 mg of pyridine and 54 mg of 3,5-dinirobenzoyl chloride, and the mixture was warmed at 30° to 40° C. for 30 minutes. A portion of the solution was taken and analyzed by high performance liquid chromatography (column: OA-4200 (Sumitomo Chemcal), 4.6 mm×250 mm; solvent: n-hexane/1,2-dichloroethane/ethanol =10:0.9:0.1; flow rate: 1.0 ml/min).

The second aspect of the present invention, which is concerned with the optical resolution of a (±)-3-alkyl-3,4-dihydro-2H-[1,4]benzoxazine derivative of general formula (II), is described in detail below.

The present inventors have conducted extensive investigations to develop a method for optical resolution of racemic compound (II). It is the characteristic feature of this method that the resolution reagent is less expensive and readily recovered.

As is apparent from the structure, both compounds (II) and (IV) have one asymmetric carbon in each melolecule. Compound (II) is composed of two enantiomeric isomers, and compound (IV) is also composed of two enantiomeric isomers. Four diastereoisomeric salts can be derived by combining the enantiomeric isomer of compound (II) and enantiomeric isomer of compound (IV). The present inventors found that two salts among these four salts were less soluble in organic solvents and readily precipitated from the solvents.

As a result, it has been found that only one of two optical isomers of compound (II) can be selectively precipitated in the form of a crystalline salt (V) according to the kind of camphor-10-sulfonic acid (IV), when a racemic mixture of compound (II) and one of the optically active compound (IV) is added in a solvent.

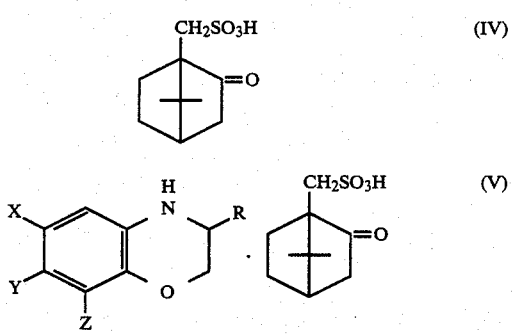

It was further found that the resolution reagent can be recovered in good yield and high purity.

When racemic compound (II) and one optical isomer of compound (IV) are dissolved thoroughly in a solvent of aqueous carboxylic acid, then a salt of one isomer of compounds (II) and (IV) is made to precipitate from the solution. On the other hand, when the other isomer of compound (IV) is used as the resolution reagent, the other isomer of compound (II) is precipitated in the form of salt. These facts show that the salts having the specific combination of optical isomers readily precipitate. The salts which readily precipitate have the following combination of the optical isomers of compounds (II) and (IV) as shown in Table 1 below.

TABLE 1

| Combination of the Optical Isomers of (II) and (IV) Obtained as Precipitated Salt | |
|---|---|
| Compound (IV) | Compound (II) |
| (R)-(−)-camphorsulfonic acid | (S)—(−)-isomer of compound (II) |
| (S)—(+)-camphorsulfonic acid | (R)-(+)-isomer of compound (II) |

As shown in Table 1 above, for the purpose of isolating (S)-isomer of compoud (II), (R)-camphorsulfonic acid is the suitable resolution reagent, and for the isolation of (R)-isomer of compound (II), (S)-camphorsulfonic acid is suitable.

The optical purity of the precipitated salt is increased by repetition of recrystallization. The free optically active compound can be obtained by treating the isolated salt with a base and successive extraction with an organic solvent. The optical purity of the salt is maintained even after the treatment with a base. Moreover, the optical resolution reagent (IV) can be recovered in good yield and purity from the aqueous phase after treatment of salt (V) with a base.

The preparation of salt (V) is initiated either by adding the racemic compound (II) and specific optical isomer of compound (IV) to a solvent or by mixing a solution of racemic compound (II) dissolved in a carboxylic acid solvent with an aqueous solution of the specific isomer of compound (IV).

After the above mixing, the mixture is stirred at 70° to 100° C. for a period ranging from 30 minutes to 1 hour for the completion of dissolution and, then, further stirred under ice-cooling at 5° to 10° C. for 2 to 18 hours for crystallization of salt (V). For the repetition of recrystallization of salt (V), seed crystals may have to be added when hardly crystallized in an early stage but the crystallization becomes progressively easier as the recrystallization procedure is repeated.

In the above practice of the present invention, it is generally advantageous to mix compounds (II) and (IV) in equimolar ratio.

As for the solvent of this resolution method, carboxylic acid such as acetic acid, propionic acid and butyric acid are preferable. The most preferable one is acetic acid, and especially acetic acid with a water content of from 10 to 50% (v/v) is beneficial for the purpose.

The amount of the solvent is preferably in the range of 5 to 20 parts (v/w), and more preferably in the range of 10 to 20 parts (v/w), based on compound (II). The crystallized salt (V is collected by filtration, washed with a small quantity of the same solvent as used in the reaction or a different inert organic solvent such as ether, and dried.

The salt obtained can be simply treated with a base and extracted with an organic solvent to give the free optically active compound in high optical purity. The base may be organic or inorganic only if it is a stronger base compared with compound (II) and is preferably an inorganic base such as the hydroxides, carbonates and hydrogen carbonates of sodium, potassium and so on. As the solvent used for extraction, a halogenated hydrocarbon such as dichloromethane, chloroform, 1,2-dichloroethane, etc., are preferred.

The optical purity of the product can be determined by high performance liquid chromatography (HPLC) as described above (see, for example, EP-A-206,283 and JP-A-62-87577). The optical purity of compound (II) after 3 to 4 recrystallization runs was more than 98% e.e.

The yield of the optically active compound can be increased by recycling of the recrysallization mother liquid or the second crop of crystals and is not less than 30% based on starting compound (II).

The optical resolution reagent compound (IV) can be easily recovered in the following manner. The aqueous layer after isolation of the free optically active compound or the aqueous layer which may be obtained after extracting the benzoxazine compound (II) by the method as stated above from a salt mixture predominantly composed of undesired optical isomer of compound (II) is first acidified, concentrated if desired, and extracted with an organic solvent such as chloroform, 1,2-dichloroethane or the like. The compound (IV) thus recovered gave melting point, optical rotation and other physical values in agreement with the known values, indicating that the compound can be recovered in high purity. When the recovered compound (IV) was again used in the optical resolution procedure, no deterioration in the efficiency of resolution was observed at all.

The construction and effects of the present invention are now illustrated in greater detail with reference to specific examples, which are not to be construed as limiting the scope of the present invention.

EXAMPLE 1

7,8-Difluoro-3-methyl-2H-[1,4]benzoxazine (I, X=H, Y=Z=F, R=CH₃):

In a nitrogen stream, a solution of 2.11 ml of t-butyl hypochlorite and 2 ml of ethyl acetate were added dropwise to a mixture of 1.54 g of (R)—(+)-7,8-difluoro-3-methyl-3,4-dihydro-2H-[1,4]benzoxazine (optical purity: 71.7% e.e., (R)), 5.21 ml of triethylamine and 9 ml of ethyl acetate while keeping the internal temperature at −52° C. over a period of about 4 minutes, and the resulting mixture was further stirred at −60° to −50° C. for 30 minutes. The reaction mixture was washed twice with 10 ml portions of 5% aqueous solution of citric acid and further with 10 ml of dilute aqueous ammonia (concentrated aqueous ammonia:-water=1:4 (v/v)) and the ethyl acetate layer was dried over anhydrous magnesium sulfate. The ethyl acetate was removed under reduced pressure and the oily residue was purified over silica gel (50 g) column chromatography using chloroform (the bottom layer after shaking with concentrated aqueous ammonia) as the eluent. The solvent was removed from the eluate under reduced pressure to yield 693 mg of 7,8-difluoro-3-methyl-2H-[1,4]benzoxazine as pale yellow crystals (yield: 60.8%).

Melting Point: 51.2° C. (Metler FP-61 automatic melting point meter, temperature increment: 1° C./minute)

Elemental Analysis for $C_9H_7F_2NO$:

| Calc'd: | C, 59.02; | H, 3.85; | N, 7.65 |
|---|---|---|---|
| Found: | C, 58.91; | H, 3.89; | N, 7.49 |

NMR (CDCl$_3$)δ ppm:
2.12 (3H, s, —C$\underline{H}_3$), 4,56 (2H, s, OC$\underline{H}_2$—), 6.5–7.2 (2H, m, benzene ring-$\underline{H}$) MS (m/Z): 183 (M+)

EXAMPLE 2

7,8-Difluoro-3-methyl-3,4-dihydro-2H-[1,4]benzoxazine (II, X=H, Y=Z=F, R=CH$_3$):

A mixture of 641.3 mg of 7,8-difluoro-3-methyl-2H-[1,4]benzoxazine obtained in Example 1, 0.32 g of 5% palladium-on-carbon (50% aqueous) and 13 ml of ethanol was subjected to catalytic reduction in a hydrogen gas atmosphere at room temperature under atmospheric pressure. After completion of the reaction, the catalyst was filtered off and the ethanol was removed under reduced pressure. The residue was dissolved in 20 ml of ethyl acetate, washed with 5 ml of saturated aqueous solution of sodium chloride and dried over anhydrous magnesium sulfate. After the desiccant was filtered off, the solution was concentrated to approximately one-half of the initial volume and to the concentrate was added 0.31 ml of concentrated hydrochloric acid was stirring. After ice-cooling, the resulting crystals were collected by filtration and washed with cold ethyl acetate to give 554.5 mg of 7,8-difluoro-3-methyl-3,4-dihydro-2H-[1,4]-benzoxazine hydrochloride as colorless crystals (yield: 71.5%).

Melting Point: 180.7° C. (determined with a Metler FP-61 automatic melting point meter, temperature increment 1° C./minute)

Elemental Analysis for $C_9H_{10}ClF_2NO$:

| Calc'd: | C, 49.02; | H, 4.61; | N, 6.38 |
|---|---|---|---|
| Found: | C, 48.77; | H, 4.55; | N, 6.32 |

NMR (DMSO-d$_6$)δppm: 1.45 (3H, d, —C$\underline{H}_3$), 3.6–4.0 (1H, m, NC$\underline{H}$<), 4.22, 4,56 (each 1H, q, OC$\underline{H}_2$—), 6.8–7.3 (2H, m, benzene ring-H)

Optical Purity: 0.5% e.e., (R), 3S:3R =0.99:1.00

EXAMPLE 3

7,8-Difluoro-3-methyl-3,4-dihydro-2H-[1,4]benzoxazine (II, X=H, Y=Z=F, R=CH$_3$):

A solution of 1.154 g of (R)−(+)-7,8-difluoro-3-methyl-3,4-dihydro-2H-[1,4]benzoxazine (optical purity: 71.7% e.e., (R)), 9 ml of ethyl acetate and 5.21 ml of triethylamine was cooled to −50° C. or less in a nitrogen gas stream. To this was added a solution of 2.11 ml of t-butyl hyopchlorite in 5 ml of ethyl acetate cooled to −50° C. or less over a period of about 20 seconds. The mixture was stirred at −60° to −50° C. for further an hour, then washed twice with 10 ml portions of cold 5% aqueous citric acid solution and 10 ml of cold dilute aqueous ammonia (the same as mentioned hereinbefore).

To the ethyl acetate layer were added 0.47 g of sodium borohydride and 2 ml of ethanol, and the mixture was stirred at room temperature for 2 hours. The reaction mixture was washed twice with 10 ml portions of 5% aqueous citric acid solution and once with 10 ml of dilute aqueous ammonia (the same as mentioned hereinbefore), and dried over anhydrous magnesium sulfate. The desiccant was filtered off and to the solution was added with 0.72 ml of concentrated hydrochloric acid with stirring. After cooling with ice-water, the resulting crystals were collected by filtration and washed with cold ethyl acetate to give 1.236 g of 7,8-difluoro-3-methyl-3,4-dihydro-2H-[1,4]benzoxazine hydrochloride as colorless crystals. Optical purity: 1.0% e.e., (S), 3S:3R =1.02:1.00. In 10 ml of chloroform was suspended 1.078 g of the above hydrochloride and to the suspension was added 10 ml of 5% aqueous sodium hydrogen carbonate solution with stirring. The chloroform layer was washed with water and dried over anhydrous magnesium sulfate. Then, the desiccant was filtered off and the solvent was distilled off under reduced pressure. The residue was dissolved in 1 ml of methanol, followed by addition of 5 ml of 50% aqueous methanol. After cooling with ice-water, the resulting crystals were collected by filtration to give 0.596 g of the title compound (yield: 60.9%).

Melting Point 51.0° C. (Metler FP-61 automatic melting point meter, temperature increment: 1° C./minute)

Elemental Analysis for $C_9H_9F_2NO$:

| Calc'd: | C, 58.38; | H, 4.90; | N, 7.56 |
|---|---|---|---|
| Found: | C, 58.36; | H, 5.06; | N, 7.64 |

EXAMPLE 4

7,8-Difluoro-3-methyl-3,4-dihydro-2H-[1,4]benzoxazine (II, X=H, Y=Z=F, R=CH$_3$):

A mixture of 1.154 g of (R)-(+)-7,8-difluoro-3-methyl-3,4-dihydro-2H-[1,4]benzoxazine (optical purity: 71.7% e.e., (R)), 5.21 ml of triethylamine and 5.8 ml of N,N-dimethylformamide was cooled to -60 to -50° C. under a nitrogen gas stream. To this solution was added 1.00 g of N-chlorosuccinimide (NCS) and the mixture was stirred at the same temperature for 35 minutes. Then, 047 g of sodium borohydride was added thereto and the mixture was stirred at room temperature for 20 minutes. The reaction mixture was diluted with 50 ml of ethyl acetate, washed twice with 10 ml portions of 5% aqueous citric acid solution and once with 10 ml of dilute aqueous ammonia (described hereinabove), and dried over anhydrous magnesium sulfate. The desiccant was then filtered off and the filtrate was concentrated to about 30 ml. To the concentrate was added 0.72 ml of concentrated hydrochloric acid and after cooling with ice-water, the resulting crystals were collected by filtration. The procedure gave 0.984 g of hydrochloride of the title compound (yield: 51.4%). Optical Purity: 7.6% e.e., (R), 3R:3S =1.00:0.86

EXAMPLE 5

To 10 ml of 20% aqueous acetic acid were added 1 g of (±)-7,8-difluoro-3-methyl-3,4-dihydro-2H-[1,4]-benzoxazine (hereinafter, referred to as "(±)-FBO") and 1.35 g of (R)-(−)-camphor-10-sulfonic acid monohydrate (hereinafter, referred to as "R-CSA"), and the mixture was stirred at 70° to 80° C. for dissolution. Then, the solution was further stirred under ice-cooling at 5° to 10° C. for 3 hours for crystallization. The procedure gave 1 g of crystals (yield: 46% based on (±)-FBO).

The above crystals were treated with aqueous sodium hydroxide solution and then extracted with dichloroethane. The extract was concentrated to dryness and the optical purity of the residue was determined by HPLC method. Optical purity: 49.2% e.e. The relationship of yield (based on (±)-FBO) and optical purity with the various water contents of the solvent is shown below in Table 2.

TABLE 2

| The Relationship of yield and optical purity with the water content of the solvent | | |
|---|---|---|
| Water Content of Solvent (%) | Yield (%) | Optical Purity (% e.e.) |
| 10 | 73 | 15.6 |
| 20 | 46 | 49.2 |
| 30 | 60 | 27.5 |

EXAMPLE 6

To 120 ml of 20% aqueous acetic acid solution were added 10 g of (±)-FBO and 13.5 g of R-CSA and the mixture was treated as in Example 5 to give crystals. The recrystallization procedure was repeated twice to yield 3.34 g of crystals.

Melting Point: 215°–218° C. $[\alpha]_D$-42.9° (c=1.0, methanol)

Elemental Analysis for $C_{19}H_{25}F_2NO_5S$;

| | | | |
|---|---|---|---|
| Calc'd: | C, 54.66; | H, 6.04; | N, 3.35 |
| Found: | C, 54.61; | H, 6.22; | N, 3.22 |

The crystals obtained were treated with aqueous sodium hydroxide solution and extracted in the same manner as described above, and the extract was concentrated to give 1.48 g of oily residue. (Yield: 14.8% based on (±)-FBO). The physical data of this oily product, e.g., analytical data of IR, NMR, GC, TLC, etc., were identical to those reported in EP-A-206,283. The optical purity of the product was 98% e.e.

EXAMPLE 7

The procedure of Example 6 was repeated except that recrystallization was repeated 4 times, and the crystallization mother liquid (ML) and second crop of crystals were recycled to the next lot (see the flow diagram as shown in FIG. 1). As a result, (−)-FBO was obtained in Run 3 with a yield of 30% and an optical purity of 99% e.e.

EXAMPLE 8

To 9 ml of 20% aqueous acetic acid were added 0.74 g of (±)-FBO and 1.0 g of the recovered R-CSA, and the same crystallization procedure as described above was carried out to yield 0.9 g of crystals. The yield was 54%. This product was treated with aqueous sodium hydroxide solution and free compound was extracted in the same manner as in Example 5. After this procedure, the optical purity was 59.5% e.e., which was not low as compared with the purity obtained using a fresh lot of R-CSA.

EXAMPLE 9

To 13 ml of 15% aqueous acetic acid were added 555 mg of (±)-FBO and 750 mg of (S)-(+)-camphor-10-sulfonic acid monohydrate, and the same crystallization procedure as described above was followed to give 0.23 g of crystals (Yield: 17.6%).

Melting Point: 215°–218° C.

$[\alpha]_D$+43.3° (c=1.0, methanol)

The product obtained was treated with aqueous sodium hydroxide solution to give the corresponding free compound and its optical purity was determined. The optical purity as (+) compound was 50% e.e. This compound was further purified. By instrumental analyses including IR and NMR spectrometric determinations, the product was identified to be (R)-(+)-7,8-difluoro-3-methyl-3,4-dihydro-2H-[1,4]benzoxazine.

While the invention has been described in detail and with reference to specific embodiments thereof, it will be apparent to one skilled in the art that various changes and modifications can be made therein without departing from the spirit and scope thereof.

What is claimed is:

1. A salt of an (S)-3-alkyl-benzoxazine derivative with (R)-(−)-camphor-10-sulfonic acid which has the general formula (V)'

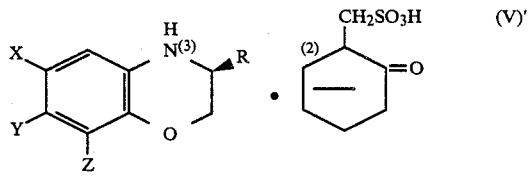

wherein X, Y and Z, which may be the same or different, each represents a hydrogen atom or a halogen atom and R represents a lower alkyl group having 1 to 6 carbon atoms.

2. The salt as claimed in claim 1, wherein X is a hydrogen atom, Y and Z each is a fluorine atom and R is a methyl group.

3. A process for producing an optically active benzoxazine compound which comprises subjecting a (±)-3-alkyl-3,4-dihydro-2H-[1,4]benzoxazine derivative of the general formula (II)

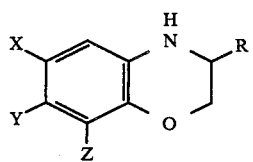 (II)

wherein X, Y and Z, which may be the same or different, each represents a hydrogen atom or a halogen atom and R represents a lower alkyl group having 1 to 6 carbon atoms, to optical resolution using an optically active form of camphor-10-sulfonic acid as an optical resolution reagent.

4. The process as claimed in claim 3, wherein X is a hydrogen atom, Y and Z each is a fluorine atom and R is a methyl group.

* * * * *

UNITED STATES PATENT AND TRADEMARK OFFICE
CERTIFICATE OF CORRECTION

PATENT NO. :  4,880,926

DATED :  November 14, 1989

INVENTOR(S) :  FUJIWARA

It is certified that error appears in the above-identified patent and that said Letters Patent is hereby corrected as shown below:

On the title page, in item [75]:
    Delete Hideaki Tsurumi as an inventor.

In columns 2 and 10, delete formula (V)' and insert formula (V)' as corrected:

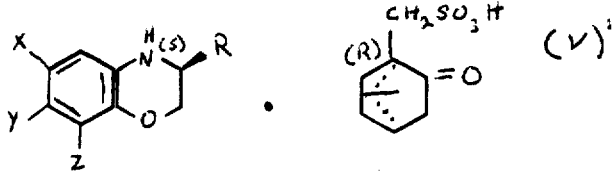

Column 2, delete formula (III) and insert formula (III) as corrected below:

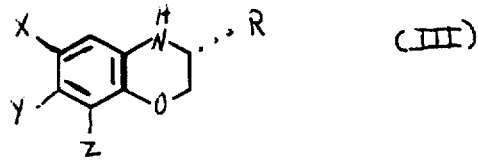

Column 1, line 53; column 2, line 40; column 2, line 57; column 7, line 53; and column 9, line 11, delete "[1,4]-benzo" among the descriptions and insert -- [1,4]benzo -- (delete hyphen).

Column 6, line 12, delete "salt '(V ' " and insert -- salt '(V)' --.

UNITED STATES PATENT AND TRADEMARK OFFICE
CERTIFICATE OF CORRECTION

PATENT NO. : 4,880,926

DATED : November 14, 1989

INVENTOR(S) : FUJIWARA

It is certified that error appears in the above-identified patent and that said Letters Patent is hereby corrected as shown below:

Column 8, line 63, delete "047 g" and insert -- 0.47 g --.

Signed and Sealed this

Twenty-first Day of January, 1992

*Attest:*

HARRY F. MANBECK, JR.

*Attesting Officer*      *Commissioner of Patents and Trademarks*